US007097145B2

(12) United States Patent
Turner (10) Patent No.: US 7,097,145 B2
(45) Date of Patent: Aug. 29, 2006

(54) SUPPORT ARM FOR A SURGICAL THEATER SYSTEM (75) Inventor: Jonathan D. Turner, Dillsboro, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 178 days.

(21) Appl. No.: 10/489,555

(22) PCT Filed: Sep. 14, 2001

(86) PCT No.: PCT/US01/28731

§ 371 (c)(1),
(2), (4) Date: Mar. 11, 2004

(87) PCT Pub. No.: WO03/025453

PCT Pub. Date: Mar. 27, 2003

(65) Prior Publication Data
US 2004/0188578 A1 Sep. 30, 2004

(51) Int. Cl.
A47F 5/00 (2006.01)
F16M 11/00 (2006.01)
F16M 13/00 (2006.01)

(52) U.S. Cl. .............................. 248/281.11; 248/274.1; 248/276.1; 248/280.11; 248/282.1 A (58) Field of Classification Search ............ 248/280.11, 248/281.11, 282.1, 284.1, 317, 343, 919, 248/323, 325, 326
See application file for complete search history.

(56) References Cited

U.S. PATENT DOCUMENTS

| 860,303 A | 7/1907 | Jones |
| 1,686,341 A | 10/1928 | Nathanson |
| 2,287,577 A * | 6/1942 | Stava .................. 248/586 |
| 2,547,532 A | 4/1951 | Mendelsohn |
| 2,911,519 A | 11/1959 | Phillips et al. |
| 2,941,776 A * | 6/1960 | Lauterbach ............ 248/280.11 |
| 3,000,606 A | 9/1961 | Storm, Jr. et al. |
| 3,010,013 A | 11/1961 | Gunther et al. |
| 3,012,781 A | 12/1961 | Nelson |
| 3,240,925 A | 3/1966 | Paschke et al. |
| 3,272,928 A | 9/1966 | Hainzelin |
| 3,360,640 A | 12/1967 | Seitz et al. |

(Continued)

FOREIGN PATENT DOCUMENTS

DE  1112023  8/1961

(Continued)

OTHER PUBLICATIONS

Physiological Monitoring Management Systems—Track Mounted Suspension Arms, Medaes Architectural & Engineering Systems brochure, five pages, date unknown.

(Continued)

Primary Examiner—Amy J. Sterling
(74) Attorney, Agent, or Firm—Barnes & Thornburg LLP (57) ABSTRACT A surgical theater system includes a boom rotating about a hub and coupled to a counterbalance arm assembly having a counterbalance arm and a monitor mount assembly configured to permit a monitor or other device to be positioned horizontally and vertically within a surgical suite and maintain the vertical elevation selected. The counterbalance arm includes a proximal hub, a first parallel link, a second parallel link, a spring link, a spring and a distal hub. First, second and third proximal pivot axes extend through the proximal hub with the third pivot axis being movable along a radial line forming an angle with a line intersecting the first and second proximal pivot axes. The spring link is coupled to the third proximal pivot axis, spring and second parallel link.

10 Claims, 9 Drawing Sheets

U.S. PATENT DOCUMENTS

| | | | |
|---|---|---|---|
| 3,584,793 A | 6/1971 | Ilzig et al. | |
| 3,783,262 A | 1/1974 | Pile | |
| 3,820,752 A | 6/1974 | Oram | |
| 3,936,671 A | 2/1976 | Bobrick et al. | |
| 4,032,775 A | 6/1977 | Bobrick et al. | |
| 4,080,530 A | 3/1978 | Krogsrud | |
| 4,082,244 A | 4/1978 | Groff | |
| 4,097,919 A | 6/1978 | Bobrick et al. | |
| 4,107,769 A * | 8/1978 | Saluja | 362/402 |
| 4,130,858 A | 12/1978 | Hayakawa | |
| 4,160,536 A | 7/1979 | Krogsrud | |
| 4,165,530 A | 8/1979 | Sowden | |
| 4,166,602 A | 9/1979 | Nilsen et al. | |
| 4,208,028 A | 6/1980 | Brown et al. | |
| 4,266,747 A | 5/1981 | Souder, Jr. et al. | |
| 4,390,932 A | 6/1983 | Matsui et al. | |
| 4,447,031 A | 5/1984 | Souder, Jr. et al. | |
| 4,453,687 A | 6/1984 | Sweere | |
| 4,494,177 A | 1/1985 | Matthews | |
| 4,517,632 A | 5/1985 | Roos | |
| 4,523,732 A | 6/1985 | Biber et al. | |
| 4,692,849 A | 9/1987 | Le Vantine | |
| 4,744,019 A | 5/1988 | Krogsrud | |
| 4,770,384 A | 9/1988 | Kuwazima et al. | |
| 4,836,478 A | 6/1989 | Sweere | |
| 4,844,387 A | 7/1989 | Sorgi et al. | |
| 4,846,434 A | 7/1989 | Krogsrud | |
| 4,953,822 A * | 9/1990 | Sharber et al. | 248/281.11 |
| 5,025,359 A | 6/1991 | Saluja et al. | |
| 5,038,261 A | 8/1991 | Kloos | |
| 5,108,063 A | 4/1992 | Koerber, Sr. et al. | |
| 5,165,786 A * | 11/1992 | Hubert | 362/287 |
| 5,186,337 A | 2/1993 | Foster et al. | |
| 5,277,427 A | 1/1994 | Bryan et al. | |
| 5,333,103 A | 7/1994 | Cvek | |
| 5,340,072 A | 8/1994 | Halbirt | |
| 5,348,260 A | 9/1994 | Acevedo | |
| 5,603,496 A | 2/1997 | Rappaport | |
| 5,618,090 A | 4/1997 | Montague et al. | |
| 5,826,846 A | 10/1998 | Buccieri et al. | |
| 6,012,693 A | 1/2000 | Voeller et al. | |
| 6,012,821 A | 1/2000 | Yeaney et al. | |
| 6,132,062 A | 10/2000 | Borders et al. | |
| 6,176,597 B1 | 1/2001 | Smith | |
| 6,328,458 B1 | 12/2001 | Bell et al. | |
| 6,402,351 B1 | 6/2002 | Borders et al. | |
| 6,443,596 B1 | 9/2002 | Bulko et al. | |
| 6,639,623 B1 | 10/2003 | Howell et al. | |

FOREIGN PATENT DOCUMENTS

| | | |
|---|---|---|
| DE | 8309857.7 | 11/1986 |
| DE | 3714637 | 12/1988 |
| EP | 0312355 A2 | 4/1989 |
| EP | 0508178 | 10/1992 |

OTHER PUBLICATIONS

Ergotron® Inc., Ergotron Computer Mounting Solutions, 1995.
Ergotron® Inc., Computer WorkCenters and LAN Racking Systems, Catalog No. FLC. Jan. 1, 1994.
Ergotron® Inc., Your Total Computer Management Solution for Manufacturing Automation, date unknown.
Ergotron® Inc., Command Post™ Adjustable Systems, Brochure No. CPS Jan. 15, 1995.
Ergotron® Inc., Power Lift 2000™ Computer WorkCenter, Catalog No. POW Feb. 25, 1995.

* cited by examiner

SUPPORT ARM FOR A SURGICAL THEATER SYSTEM

CROSS-REFERENCE TO RELATED APPLICATIONS

This application is the U.S. national phase of international application serial no. PCT/US01/28731 filed Sep. 14, 2001.

BACKGROUND AND SUMMARY

This invention relates generally to support arms for surgical theater systems and more particularly to support arms having a counterbalance arm to balance the weight of the supported object so that it can be suspended at a selected height without locking the arm.

Surgical theater systems are floor, wall, or ceiling mounted systems including devices which can be positioned in desired locations within a surgical suite to maximize there accessibility, utility, and/or viewability. Examples of surgical light systems can be found in U.S. Pat. Nos. 6,012,821 and 6,132,062 and U.S. applications Ser. Nos. 09/050,265; 09/050,529; 09/050,534 and 09/747,605 which are expressly incorporated herein by reference. Such surgical theater systems support devices such as surgical lights, monitors, cameras, and electronic instruments utilized by surgeons and operating room personnel during the performance of surgical procedures. The above identified patents demonstrate that it is well known to provide surgical theater systems which facilitate the positioning, both horizontally and vertically, of the devices attached thereto to maximize their utility. In order to maintain the proper orientation in space of the device mounted to the counterbalance arm, the counterbalance arm includes a parallelogram linkage.

U.S. application Ser. No. 09/747,605 shows a surgical theater system with a counterbalance arm which seeks to minimize vertical movement of a device after it has been positioned at a desired height by providing a counterbalance arm having frictional brakes engaging pivot pins about which the arm rotates. Counterbalance arms are well known devices incorporating counterweights or spring mechanisms which provide a vertical upward force to the distal end of a cantilevered arm to counteract the downward force exerted on the distal end of the cantilevered arm by the object supported. The forces create torques about the lower pivot axis of the counterbalance arm. Ideally, the torque exerted on the counterbalance arm will be equal in magnitude to, but Opposite in direction to, the torque exerted on the counterbalance arm by the weight. Recognizing that the ideal situation cannot always be achieved, U.S. application Ser. No. 09/747,605 compensates for the inequalities by applying a frictional force to the pivot axis which permits the torques of the weight and the spring members to be slightly unbalanced.

The torque exerted by a weight hanging freely suspended from a fixed point on an arm is proportional to the sine of the angle formed between the vertical plane and the longitudinal axis of the arm. Thus the greatest torque is exerted by an object freely hanging from a fixed point on a beam when the longitudinal axis of the beam is horizontal, sin 90 deg=1.

Springs and gas springs typically obey Hooke's law, at least while in the region of elasticity, so that the force exerted by the spring is proportional to its displacement from equilibrium. In counterbalance arms, the spring is typically not mounted perpendicular to the longitudinal axis of the arm but rather couples to the distal end of the arm and to an end of a spring link. The spring link is typically pivotally mounted at a first end to a fixed location relative to the pivot axis of the proximal end of the counterbalance arm and mounted at the other end to slide within a slot formed in the counterbalance arm. The spring is typically pivotally mounted to the sliding end of the spring link and pivotally mounted to the second end of the counterbalance arm. Thus the spring exerts a force directed substantially along the longitudinal axis which is converted by the spring link into components of force parallel to and perpendicular to the longitudinal axis of the spring link. The component parallel to the longitudinal axis creates strain along the link which is assumed to be incompressible. The component perpendicular to the longitudinal axis of the spring link induces the pivot pin sliding in the slot into engagement with the upper edge of the slot so that the perpendicular component reduces to a component perpendicular to the longitudinal axis of the counterbalance arm and a component parallel to the longitudinal axis of the counterbalance arm. In the disclosed embodiment of a counterbalance arm, second parallel link is formed so that a pin extends through the longitudinal slot and a roller which engages an upper wall of the second parallel link to transfer this force to the second parallel link through the roller rather than through engagement of the pin with the upper wall of the slot. The component perpendicular to the longitudinal axis of the counterbalance arm creates a torque about the pivot axis at the proximal end of the counterbalance arm which is preferably substantially equal in magnitude to, but opposite in direction to, the torque induced by the weight.

Unfortunately, gas springs do not always obey Hooke's law precisely throughout the full stroke range, so it is difficult to design a counterbalance arm that cancels out the torque induced by the weight of the object suspended by the arm. Hooke's Law provides a linear equation relating the force exerted by an elastic medium to the displacement from equilibrium of the medium. In: gas springs the displacement can be represented by the stroke length of the piston. Hooke's Law states that force (F) of a spring is equal to the displacement of the spring from its equilibrium position (x) times a spring constant (k) or:

$F=kx$.

However, it has been found that gas springs are typically manufactured so that near the ends of their stroke lengths, the gas spring is no longer operating in the linear region of the displacement v. force curve.

In accordance with one embodiment of the disclosed surgical theater system, a counterbalance arm is provided which includes an adjustment pin set at an angle to the vertical for modifying the offset of the proximal end of a spring link from the proximal end of a first parallel link so that the proximal end of the spring link is not mounted at a fixed location relative to the pivot axis at the proximal end of the counterbalance arm. The angle that adjustment pin forms with the vertical introduces a mechanical disadvantage to the spring link/spring/slot combination to compensate for increased spring forces generated when the counterbalance arm is lowered from the raised to a lowered position.

In accordance with one embodiment, the counterbalance arm includes a first parallel link, a second parallel link, a spring link and a spring. The first parallel link is mounted at the proximal end to pivot about a proximal pivot axis and mounted at a distal end to pivot around a distal pivot axis. The second parallel link is mounted at its proximate end for pivotal movement about a second proximate pivot axis and at its distal end for pivotal movement about a second distal pivot axis. The displacement between the first and second proximal pivot axes and the displacement between the first and second distal pivot axes is substantially equal to maintain the parallel relationship between the first and second parallel links. The spring link is mounted at its proximal end to pivot about a third proximal axis and at its distal end to slide relative to the second parallel link. The third proximal axis extends through a pivot pin which is movable relative to the first proximal pivot axis to adjust the displacement between the third and first proximal pivot axes.

Additional features and advantages of the support arm for a surgical theater will become apparent to those skilled in the art upon consideration of the following detailed descriptions exemplifying the best mode of carrying out the apparatus as presently perceived.

BRIEF DESCRIPTION OF THE DRAWINGS

In describing the disclosed invention reference will be made to the following drawings in which:

FIG. 6 is a cross-sectional view of the counterbalance arm in its raised position showing the adjustment screw rotated completely in a first direction to place the third proximal pivot axis extending through the proximal end of the spring links in its uppermost position;

FIG. 7 is a cross-sectional view of the counterbalance arm in its raised position showing the adjustment screw rotated completely in a second direction to place the third proximal pivot axis extending through the proximal end of the spring links in its lowermost position;

DETAILED DESCRIPTION OF THE DRAWINGS

Figure 1:
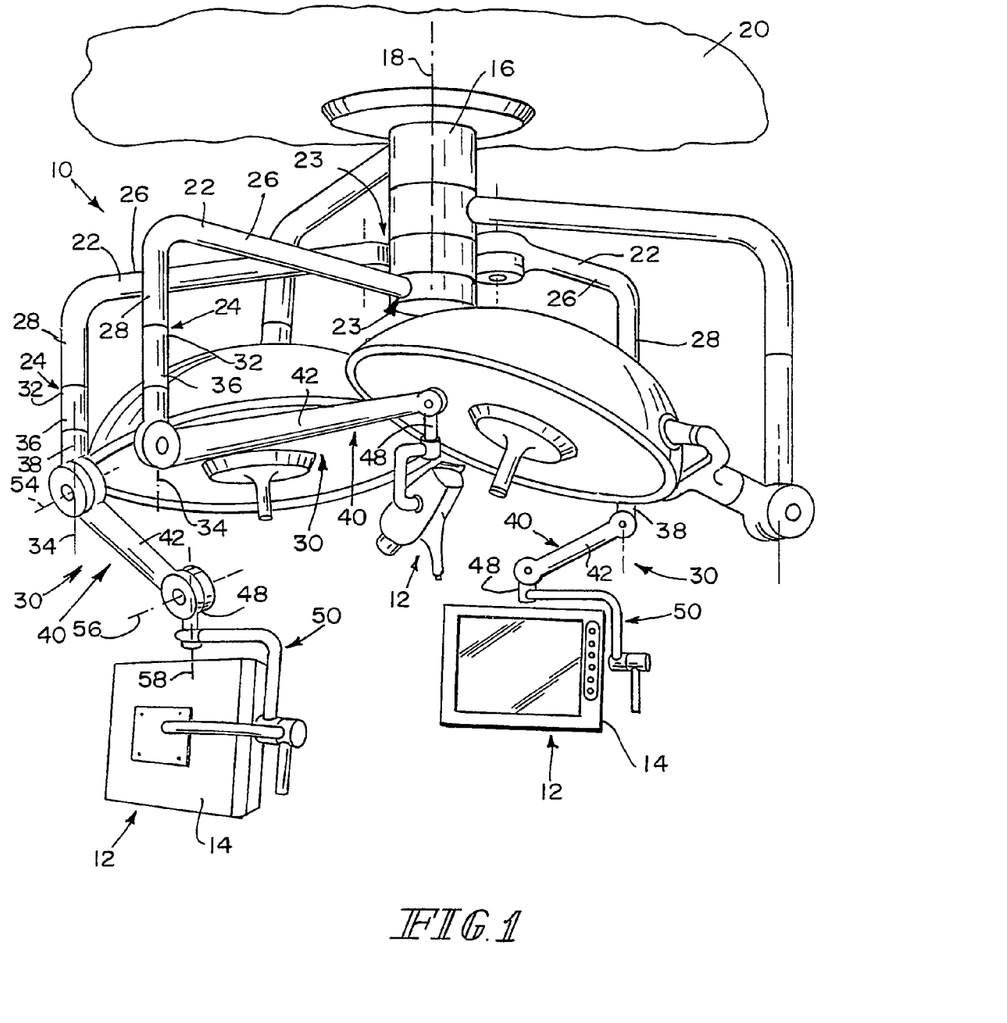
FIG. 1 is a perspective view of a surgical theater system having a monitor mounted by a monitor mount to a counterbalance arm.

A surgical theater system 10 in accordance with one embodiment of the disclosed device is provided for mounting a device 12, such as a monitor 14, within a surgical suite so that the device can be moved horizontally and vertically within the suite to facilitate maximum utilization of device 12. For example, when a monitor 14 is to be used by a surgeon during a surgical procedure, surgical theater system 10 permits monitor 14 to be positioned for optimal viewing by the surgeon without interfering with the surgical procedure. While the embodiment of the surgical theater system disclosed herein mounts a monitor 14 within a surgical suite, it is within the teaching of the disclosure for other devices 12, such as surgical lights, cameras, etc., to be mounted to surgical theater system 10 and for surgical theater system to be located in other rooms of a facility in which the device 12 is to be used.

Illustratively, surgical theater system 10 is a ceiling mount system having a central hub 16 mounted for rotation about a rotational axis 18 extending through the hub 16 and a structural support (not shown) in the ceiling 20. A boom 22 is mounted to hub 16 and includes a proximal end 23, a distal end 24, a horizontally-extending portion 26, and a vertically-extending portion 28. Boom 22 is mounted at proximal end 23 to hub 16. Horizontally-extending portion 26 extends radially from hub 16. Vertically-extending portion 28 extends downwardly from horizontally-extending portion 26 so that distal end 24 of boom 22 is horizontally and vertically displaced from hub 16. A counterbalance arm assembly 30 is mounted at its proximal end 32 to distal end 24 of boom 22 for rotation about an axis 34 extending longitudinally through vertically-extending portion 28 of boom 22.

Counterbalance arm assembly 30 includes a bearing housing 36, a proximal hub 38, a counterbalance arm 40, a distal hub or monitor pivot 48, and a monitor mount assembly 50. Counterbalance arm 40 pivots about a proximal pivot axis 54 and a distal pivot axis 56 so that a device 12 attached to monitor mount assembly 50 can be raised and lowered with respect to the boom 22. Monitor mount assembly 50 is mounted to monitor pivot 48 for rotation about rotation on axis 58 permitting monitor 14 to be positioned at a desirable location within a suite.

Figure 2:
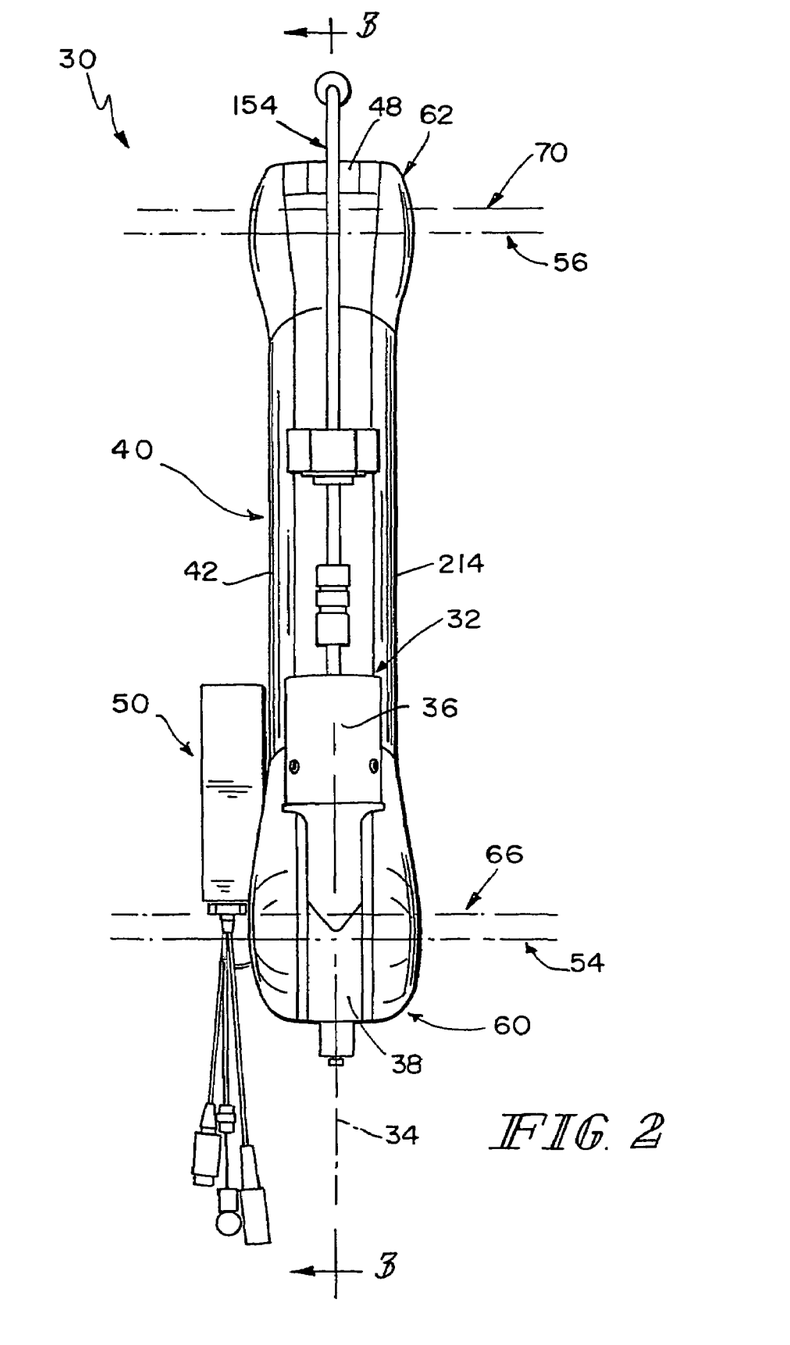
FIG. 2 is a front plan view of the counterbalance arm and monitor mount of FIG. 1.
Figure 3:
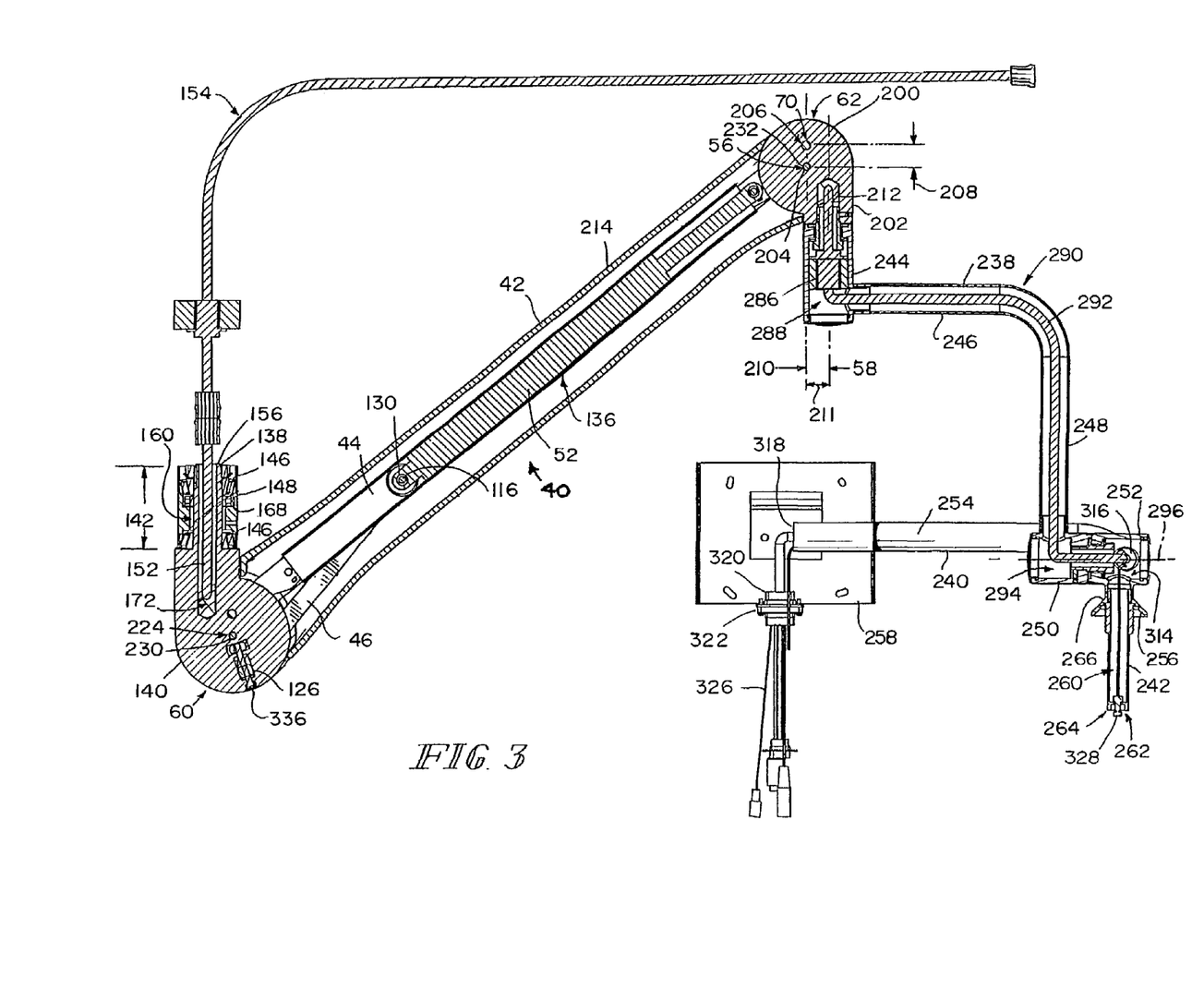
FIG. 3 is a sectional view along line 3—3 of the counterbalance arm and monitor mount of FIG. 2.

Referring to FIGS. 2 and 3, counterbalance arm 40 includes an arm housing 42 which acts in the illustrated embodiment as a first parallel link, a counterbalance arm weldment 44 which acts in the illustrated embodiment as a second parallel link, a plurality of spring links 46, and a gas spring 52. Arm housing or first parallel link 42 is mounted at its proximal end 60 to proximal hub 38 for pivotal movement relative to proximal hub 38 about a first proximal pivot axis 54. Arm housing or first parallel link 42 is mounted at its distal end 62 to distal hub or monitor pivot 48 for pivotal movement relative to monitor pivot 48 about first distal pivot axis 56. Arm weldment or second parallel link 44 is mounted at its proximal end 64 to proximal hub 38 for pivotal movement relative to proximal hub 38 about a second proximal pivot axis 66. Arm weldment or second parallel link 44 is mounted at its distal end 68 to distal hub or monitor pivot 48 for pivotal movement relative to monitor pivot 48 about a second distal pivot axis 70. A displacement 72 between first and second proximal pivot axes 54, 66 is fixed as is a displacement 74 between first and second distal pivot axes 56, 70. Because the displacements 72, 74 of the respective pivot axes 54, 66, 56, 70 are fixed, a longitudinal axis 76 of the first parallel link 42 and a longitudinal axis 78 of the second parallel link 44 are maintained substantially parallel to each other during pivotal movement of counterbalance arm 40.

Figure 5:
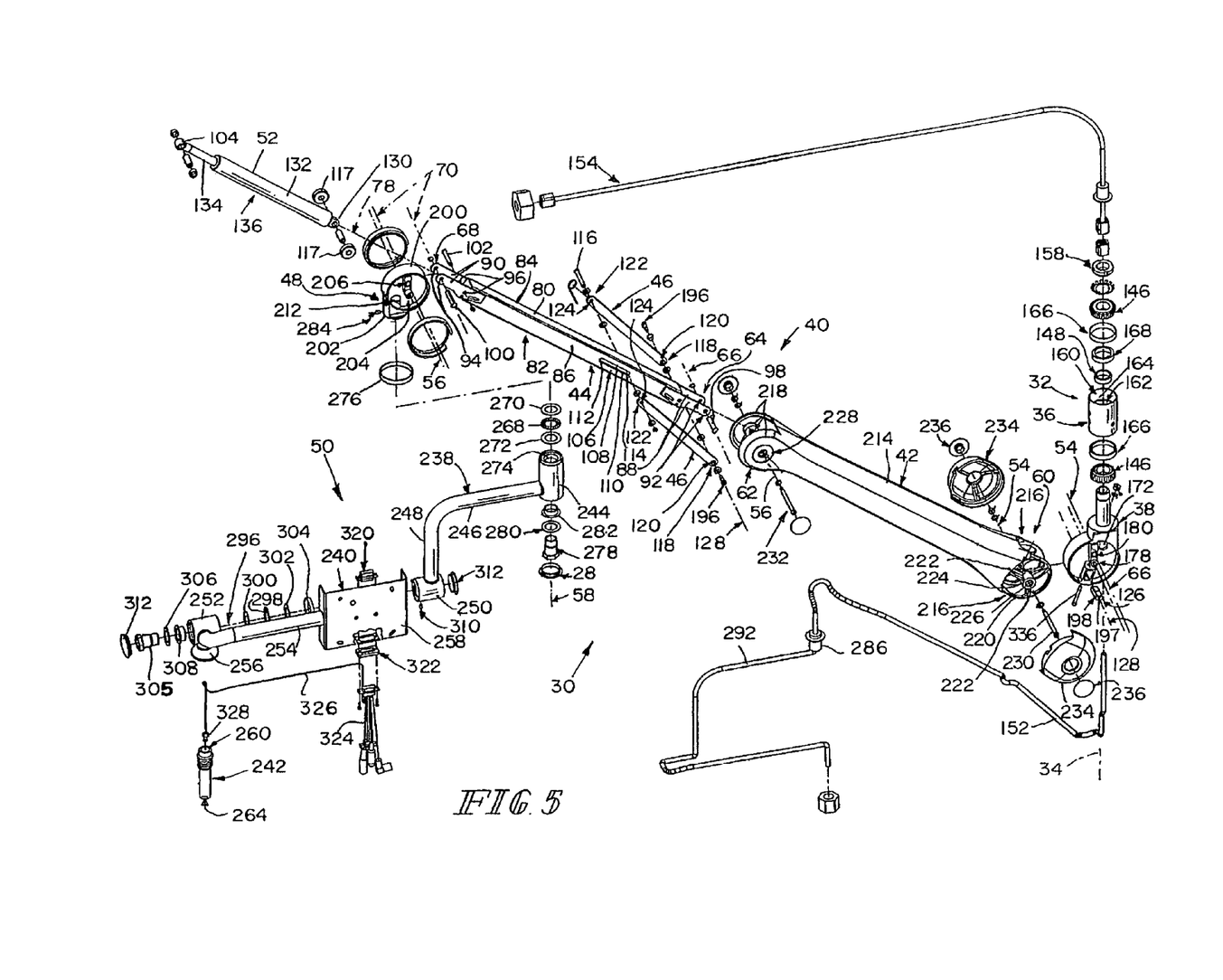
FIG. 5 is an exploded view of the counterbalance arm of FIG. 1.

Illustratively, arm weldment or second parallel link 44 is formed from a rectangular metal tube having a top wall 80, a bottom wall 82, and two side walls 84, 86 as shown in FIG. 5. Four ears 88, 90 are coupled to side walls 84, 86. Illustratively, two proximal ears 88 are attached to the side walls 84, 86 of, and extend longitudinally beyond, the tube at the proximal end 64 of arm weldment 44. Similarly, two distal ears 90 are attached to the side walls 84, 86 of, and extend longitudinally beyond, the tube at the distal end 68 of arm weldment 44. Each proximal ear 88 is formed to include a pivot pin-receiving hole 92. Each distal ear 90 is formed to include a pivot pin-receiving hole 94 and an attachment pin-receiving hole 96. A second proximal pivot pin 98 extends through pivot pin-receiving hole 92 to couple proximal end 64 of arm weldment 44 to proximal hub 38 for pivotal movement relative to proximal hub 38 about second proximal pivot axis 66. A second distal pivot pin 100 extends through pivot pin-receiving hole 94 to couple distal end 68 of arm weldment 44 to distal hub 48 for pivotal movement relative to distal hub 48 about second distal pivot axis 70. An attachment pin 102 extends through each attachment pin-receiving hole 96 and a distal end clevis 104 of gas spring 52 to pivotally couple gas spring 52 to arm weldment 44. Each side wall 84, 86 of second parallel link 44 is formed to include a longitudinally-extending slot 106 having an upper wall 108, a lower wall 110, a distal end wall 112 and a proximal end wall 114. Upper, lower, distal end and proximal end walls 108, 110, 112, 114 retain a connection pin 116 which is received for sliding movement between the proximal end wall 112 and distal end wall 114. Connection pin 116 extends through slot 106, connection pin-receiving hole 124 in spring links 46, clevis 130 of gas spring 52, and a plurality of rollers 117. Rollers 117 are sized to be received in the interior of arm weldment 44 to facilitate movement of connection pin within slot and to transfer forces exerted on connection pin through the body of roller to upper wall of arm weldment 44. While described herein as being urged against top wall 108 of slot 106 to transfer perpendicular forces to arm weldment 44, in the illustrated embodiment connection pin 116 does not engage top wall 108 of slot 106, rather connection pin 116 transfers forces to arm weldment 44 through rollers 117. While illustrated as an arm weldment 44, it is within the teaching of the disclosure for second parallel link 44 to be formed from a single link or a plurality of links.

Illustratively, each spring link 46 includes a proximal end 118 formed to include a pivot pin-receiving aperture 120 and a distal end 122 formed to include a connection pin-receiving aperture 124. A third pivot pin 126, through which a third proximal pivot axis 128 extends, is pivotally coupled to proximal end 118 of spring link 46 by shoulder bolts 196 received in each of the pivot pin-receiving apertures 120 in the proximal end of each spring link 46 and two threaded holes 197 in opposite ends of third proximal pivot pin 126. Connection pin 116 extends through each connection pin-receiving aperture 124 and through slot 106 in arm weldment 44 to slidingly couple distal end 122 of each spring link 46 to arm weldment 44. Connection pin 116 also extends through proximal end clevis 130 of gas spring 52 to pivotally couple the proximal end of gas spring 52 to spring links 46 and slidingly couple the proximal end of gas spring 52 to arm weldment 44. While the illustrated embodiment includes two spring links 46, it is within the teaching of the disclosure for a single spring link, a spring link weldment or assembly, or a plurality of spring links to be provided.

In the illustrated embodiment, a single gas spring 52 is provided. Gas springs are well known in the art and are commercially available from several sources. Illustratively, gas spring 56 is a series 16 gas spring available from Suspa Incorporated. Gas spring 52 includes a cylinder housing 132 having a clevis 130 extending from the proximal end and a rod 134 extending into the cylinder housing 132 and having clevis 104 at the distal end. Connection pin 116 extends through connection pin-receiving apertures 124 in the distal end 122 of spring links 46, slots 106 in arm weldment 44 and the clevis 130 at the proximal end of the cylinder housing 132 of the gas spring 52 to pivotally couple the gas spring 52 to the distal end 122 of the spring links 42 and slidingly couple the gas spring 52 to arm weldment 44. Connection pin 116 extends through connection pin-receiving holes 124 in the distal ears 90 of arm weldment 44 and through clevis 104 at the distal end of the rod 134 of gas spring 52 to pivotally couple the distal end of gas spring 52 to arm weldment 44 at a location between distal end wall 112 of slot 106 and distal end 68 of arm weldment 44. While the terms proximal and distal end are used in conjunction with the gas spring 52, those skilled in the art will recognize that the orientation of the gas spring 52 is not critical to the invention. The terms proximal and distal are used in this written description to indicate relative proximity, following the various arms of the surgical suite apparatus, to the mounting location. In the claims, the terms proximal and distal distinguish between portions of various components (similar to the terms "first" and "second") and are not intended to indicate proximity to any other component of a surgical theater apparatus. Also, those skilled in the art will recognize that mechanical springs, elastic material, and other materials and devices for exerting a force may be substituted for gas spring within the teaching of this disclosure. All such devices are generally referred to herein as springs 136.

The proximal hub 38 is formed to include a shaft 138 and a hub portion 140. Illustratively, shaft 138 is a tube coupled at its distal end to the hub portion 140. Shaft 138 has a length 142, best seen in FIG. 3, sufficient to extend substantially through bearing housing 36, an outside diameter 144 sized to receive two tapered roller bearings 146 and a Rulon™ bearing 148, and an inside diameter 150 sized to receive a power and signal cable 152 of a slip ring assembly 154. Illustratively, a proximal end 156 of shaft 138 is threaded to receive a locknut with key 158. Bearing housing 36 is formed to include an aperture 160 extending longitudinally therethrough. Aperture 160 includes a central bore 162 and two counterbores 164 at opposite ends of the bearing housing 36. Counterbores 164 have an inside diameter sized to receive two bearing races 166 on which the rollers of the tapered roller bearings 146 ride and a brake ring 168 against which Rulon™ bearing 148 is pulled to adjust the ease of rotation of counterbalance arm assembly 30 about rotation axis 34. Rulon™ bearing 148, brake ring 168, races 166 and tapered roller bearings 146 are secured within bearing housing 36 by a lock washer with key 170 and locknut with key 158. Cable 152 of the slip ring subassembly extends through shaft 138 and through an aperture 172 in hub portion 140 so that power and electrical signals can be conveyed to monitor 14.

Illustratively, hub portion 140 includes a disk portion 174 and a protrusion 176 to which shaft 138 is attached. Disk portion 174 is formed to include a centrally located first pivot pin-receiving hole 178, a second pivot pin-receiving hole 180 offset radially from first pivot pin-receiving hole 178, a nut-receiving aperture 182, a pivot pin-receiving aperture 184, an adjustment screw head-receiving counterbore 186, and an adjustment screw shaft-receiving bore 188. The foci of first and second pivot pin-receiving holes 178, 180 are located on a diametrical line 190 substantially parallel to rotation axis 34. Adjustment screw shaft-receiving bore 188 extends from a peripheral edge 192 of disk portion 174 radially inward through adjustment screw head-receiving counterbore 186, pivot pin-receiving aperture 184 and nut-receiving aperture 182, all of which are coaxial and concentric about a radial line 194. Third pivot pin 126 includes a longitudinal axis serving as third proximal pivot axis 128 and has an outside diameter sized to be received in pivot pin receiving aperture 184. Threaded holes 197 extend longitudinally inwardly from opposite ends of third pivot pin 126 to receive two shoulder bolts 196 which extend through pivot pin-receiving apertures 120 of spring links 46 to pivotally couple proximal ends 118 of spring links 46 to proximal hub 38 for movement about third proximal pivot axis 128. Third pivot pin 126 includes a threaded hole 198 extending radially therethrough. Third pivot pin 126 is received in pivot pin-receiving aperture 120 so that longitudinal axis 128 extends perpendicularly through disk portion 174 and threaded hole 198 is aligned with adjustment screw shaft-receiving bore 188.

Referring now again to FIG. 3, distal hub 48 includes a disk portion 200 and a mounting protrusion 202. Disk portion 200 is formed to include a first distal pivot pin-recieving hole 204 and a second distal pivot pin-receiving hole 206. Illustratively, first distal pivot pin-receiving hole 204 is concentrically located with respect to disk portion 200. Second distal pivot pin-receiving hole 206 is radially displaced from first distal pivot pin-receiving hole 204 by a displacement 208. The foci of first and second distal pivot pin-receiving holes 204, 206 are located on a diametrical line 210 substantially parallel to rotation axis 58. Mounting protrusion 202 is formed to include an aperture 212 having an inside diameter sized to receive a portion of a slip ring 214 and cable 156 of slip ring subassembly. Aperture 212 is concentric about rotation axis 58.

Arm housing 42 includes a tubular central section 214 with a pair of laterally spaced apart proximal ears 216 and a pair of laterally spaced apart distal ears 218 extending longitudinally beyond central section 214 as shown in FIG. 5. Arm housing 42 is shown as a monolithic structure but it is within the teaching of the disclosure for arm housing 42 to be formed from multiple components. Each proximal ear 216 includes an outer rim 220 coupled by a plurality of spokes 222 to a central hub 224 formed to include a first proximal pivot pin-recieving hole 226 extending therethrough. Illustratively, each distal ear 218 is cup-shaped with a central first distal pivot pin-receiving hole 228 extending therethrough. A first proximal pivot pin 230 extends through each first proximal pin-receiving hole 226 of arm housing 42 and the first proximal pivot pin-receiving hole 180 of proximal hub 38 to couple arm housing 42 to proximal hub 38 for pivotal movement about first proximal pivot axis 54. A first distal pivot pin 232 extends through each first distal pin-receiving hole 228 of arm housing 42 and the first distal pivot pin-receiving hole 204 of distal hub 48 to couple arm housing 42 to distal hub 48 for pivotal movement about first distal pivot axis 56. First proximal pivot pin 230 and first distal pivot pin 232 intersect longitudinal axis 76 of arm housing 42 so that arm housing 42 acts as a parallel link or parallel link assembly extending between first proximal pivot axis 54 and first distal pivot axis 56.

Illustratively, tubular central section 214 is sized to receive arm weldment 44, spring links 46 and gas spring 52 and their associated connecting pins and mounting hardware therein. In the illustrated embodiment arm housing 42 protects arm weldment 44, spring links 46 and gas spring 52 and their associated connecting pins and mounting hardware from the environment and permits counterbalance arm 40 to be easily cleaned. To facilitate this protective function, counterbalance arm 40 comprises two caps 234 and two plugs 236 to further enclose arm weldment 44, spring links 46 and gas spring 52 and their associated connecting pins and mounting hardware and the various pivot and connection pins coupling these various components to the proximal and distal hubs 38 and 48, respectively.

Monitor mount assembly 50 includes an upper tube monitor cradle weldment 238, a lower monitor tube/handle weldment 240 and a handle mandrel 242. Upper tube monitor cradle weldment 238 includes a proximal rotation hub 244, a horizontally extending arm portion 246, a downwardly extending arm portion 248 and a distal rotation hub 250. Lower monitor tube/handle weldment 240 includes a rotation hub 252, an L-shaped bracket arm 254, an internally threaded handle receiving hub 256, and a monitor bracket 258. Handle mandrel 242 is formed to include a longitudinally extending aperture 260 communicating with a switch-receiving hole 262 in a distal end 264. Handle mandrel 242 is externally threaded at a proximal end 266 to facilitate connection with handle receiving hub 256 of lower monitor tube/handle weldment 240.

Mounting protrusion 202 of distal hub 48 is mounted to proximal rotation hub 244 of monitor mount assembly 50 for rotational movement of monitor mount assembly 50 about rotation axis 58. To facilitate this rotational movement, thrust needle bearing 268 is sandwiched between an upper thrust washer 270 received in a cavity in the distal hub 48 of counterbalance arm 40 and a lower thrust washer 272 received in a cavity in the proximal rotation hub 244 of the monitor mount assembly 50. A bearing cover 276 is provided between distal hub 48 and proximal rotation hub 244 to protect thrust needle bearings 268. A spindle 278 extends through proximal rotation hub 244, a steel washer 280, a flanged bushing 282, thrust needle bearings 268, thrust washers 270, 272 and into the aperture 212 of distal hub 48 where it is secured by a set screw 284 to distal hub 48. A lower cap 285 is provided to cover lower end of proximal rotation hub 244. As shown, for example, in FIG. 3, a second slip ring 286 of slip ring assembly 154 is received in an aperture 288 of proximal rotation hub 244 to facilitate rotation of monitor mount assembly 50 about rotation axis 58 and transfer of signals and power through slip ring assembly 154 to monitor 14.

As shown, for example, in FIG. 3, horizontally-extending arm portion 246 and downwardly-extending arm portion 248 are tubes coupled together in an L-shape. Aperture 288 of proximal rotation hub 244 communicates with a lumen 290 of horizontally-extending arm portion 246 and downwardly-extending arm portion 248 to permit a second signal and power cable 292 of slip ring assembly 154 to extend from proximal rotation hub 244 to distal rotation hub 250. The lumen 290 of downwardly-extending arm portion 248 communicates with an aperture 294 extending horizontally through distal rotation hub 250 to permit second signal and power cable 292 of slip ring assembly 154 to extend into distal rotation hub 250.

Lower monitor tube/handle weldment 240 is mounted at rotation hub 252 to distal rotation hub 250 of upper tube monitor cradle weldment 238 to permit rotational movement of lower monitor tube/handle weldment 240 with respect to upper tube monitor cradle weldment 238 about a rotation axis 296. While mounted for rotational movement about rotation axis 296, the presence of stops (not shown) limits movement of lower monitor tube/handle weldment 240 with respect to rotation axis 296 to pivotal movement having 145 degrees of travel. Stops may be positioned to provide a greater or lesser range of pivotal motion within the teachings of the disclosure. To facilitate pivotal movement of lower monitor tube/handle weldment 240 about rotation axis 296, a thrust needle bearing 298 is sandwiched between a proximal thrust washer 300 received in a cavity in distal rotation hub 250 of upper tube monitor cradle weldment 238 and a distal thrust washer 302 received in a cavity in rotation hub 252 of lower monitor tube/handle weldment 240. A bearing cover 304 is provided between distal rotation hub 250 of upper tube monitor cradle weldment 238 and rotation hub 252 of lower monitor tube/handle weldment 240 to protect the thrust needle bearings 298. A spindle 305 extends through rotation hub 252 of lower monitor tube/handle weldment 240, a steel washer 306, a flanged bushing 308, thrust needle bearings 298, thrust washers 300, 302 and into aperture 294 of distal hub 250 of upper tube monitor cradle weldment 238 where it is secured by a set screw 310 to distal hub 250. Two end caps 312 are provided to enclose the outer ends of rotation hub 252 of lower monitor tube/handle weldment 240 and distal rotation hub 250 of upper tube monitor cradle weldment 238, respectively.

L-shaped bracket arm 254 of lower monitor tube/handle weldment 240 is illustratively comprised of tubes coupled together in an L-shape. An aperture 314 of rotation hub 252 of lower monitor tube/handle weldment 240 communicates with the a lumen 316 of L-shaped bracket arm 254 to permit second signal and power cable 292 of slip ring assembly 154 to extend from rotation hub 252 to a distal end 318 of L-shaped bracket arm 254. Signal and power cable 292 extends from distal end 318 of L-shaped bracket arm 254 and is electrically coupled to a 23-pin connector block 320. A headed pin 322 is coupled to monitor bracket 258 to facilitate attachment of a monitor cable assembly 324 to monitor bracket 258. Monitor cable assembly 324 mates with 23-pin connector block 320 50 that power and video signals can be provided to monitor 14. Illustratively, monitor cable assembly 324 includes a plurality of cables terminating in connectors adapted for attachment to inputs of a monitor 14. A control wire 326 is coupled to monitor cable assembly 324 and extends through an L-shaped bracket arm 255, rotation hub 252, handle receiving hub 256 and handle mandrel 242. Control wire 326 terminates in a switch 328 through which operation of the monitor 14 can be controlled.

Figure 4:
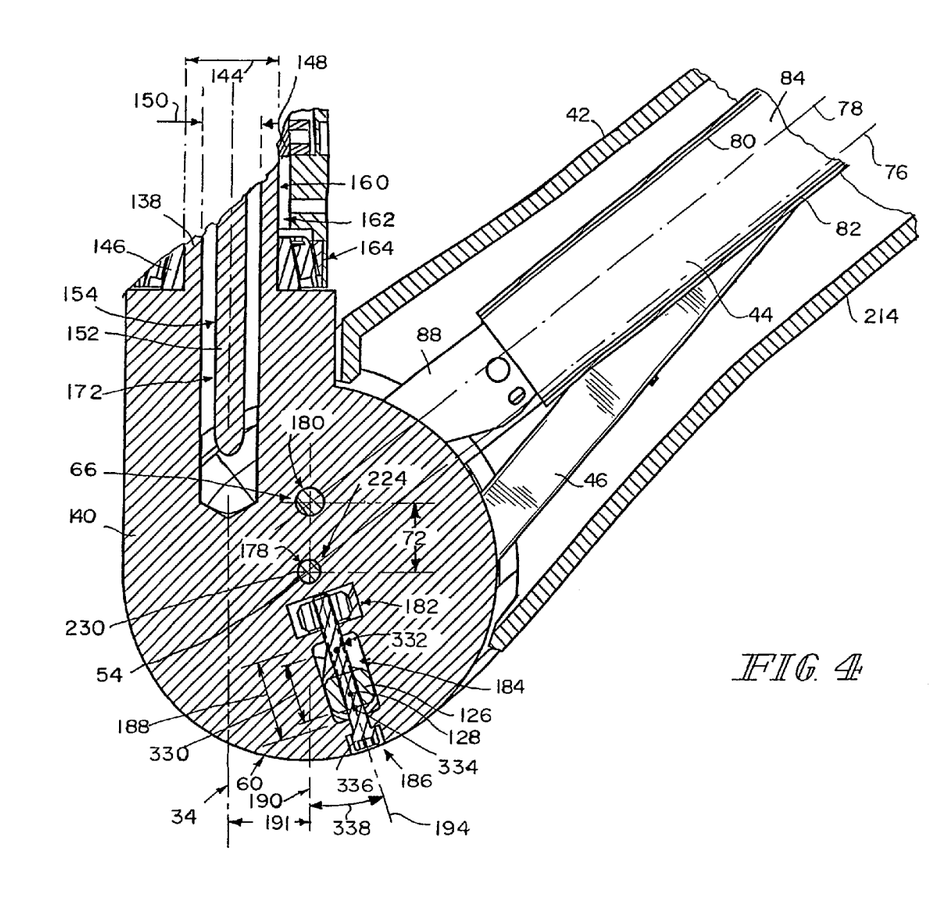
FIG. 4 is a detailed view of a portion of the counterbalance arm of FIG. 3.

As best shown in FIG. 4, third pivot axis 128 may be longitudinally moved within pivot pin-receiving aperture 184 by a distance 330 along radially extending line 194 between an uppermost position 332 and a lowermost position 334 by movement of third pivot pin 126 through rotation of an adjustment screw 336. Radial line 194 forms an angle 338 with the diametrical line 190 extending through the first and second proximal pivot axes 54, 66. Illustratively, angle 338 between radial line 194 and diametrical line 190 is approximately 18.43 degrees. When counterbalance arm 40 is moved to its raised position, gas spring 52 (coupled through spring links 46 to third pivot axis 128) exerts the strongest force when the third pivot axis 128 is located in the uppermost position 332. Conversely, when the gas spring 52 is in the raised position, gas spring 52 exerts the weakest force when the third pivot axis 128 is in the lowermost position 334. Adjustment screw 336 permits third pivot pin 126 to be moved within pivot pin-receiving aperture 184 so that third pivot axis 128 can be located anywhere between uppermost position 332 and lowermost position 334.

In the illustrated embodiment, a gas spring 52 is used which exhibits approximately a 9.5% difference in force between its initial compressed length and its full-stroke length. The angle 338 formed between the radial line 194 and the diametrical line 190 is fixed to substantially reduce, or hopefully eliminate, the difference in force exerted by the gas spring 52 as counterbalance arm is moved between its raised and lowered positions. Thus, angle 338 may be increased or decreased in accordance with the invention to facilitate other springs exhibiting different "stroke length to force" characteristics. In the illustrated embodiment, angle 338 has a measure of 18.43 degrees.

The measure of the angle 338 was determined through iterations of experiments whereby a 3-D computer generated model of counterbalance arm with a known weight attached thereto was generated using known measurements of components of counterbalance arm 40. The model was generated by introducing the arm lengths, displacements between the first and second proximal and distal pivot axes, the displacement between the top wall of slot 106 and longitudinal axis of second parallel link 44, the displacement between the pivot pin-receiving aperture and connection pin-receiving aperture 124 of spring link 42, the displacement between the diametrical line 210 and rotation axis 58 of the illustrated embodiment of counterbalance arm 40. With this computer model, the location of the third pivot axis with respect to the first and second pivot axes could be changed and the modeled arm pivoted to various locations within its pivotal range of motion. In each such position, the angle formed by spring link 42 with respect to longitudinal axis 78 of second parallel link 44 could be measured as could the location of connecting pin 116 which establishes the displacement of the rod of gas spring 52 from its equilibrium position, the length of the moment arm through which spring link 42 and gas spring generate torque, and the arm angle formed by counterbalance arm. Using these various angles and positions of components and a substantially linear force to stroke length curve for the gas spring the resultant torque on the arm for various positions could be calculated and plotted against the displacement from diametrical line 190 of third pivot axis 128. The arm was positioned in its raised position (38.68 degrees above the horizontal or 51.32 degrees from vertical). The third pivot axis 128 was moved to an initial location where a substantial equilibrium state was obtained. Then the counterbalance arm was pivoted to its lowered position (38.68 degrees below the horizontal or 128.68 degrees from the vertical). The resultant net torque on the arm in the lowered position was determined and plotted against the position of third pivot axis 128. Additional torque calculations were taken at various positions between the raised and lowered positions. A new location of third pivot axis 128 was chosen and the process repeated. Third pivot axis was moved to various locations, but only those locations which produced minimal resultant torques were plotted. A straight line was drawn through the plotted points to establish the appropriate measurement of angle 338. It is within the teaching of the disclosure for angle 338 to be determined by other methods so long as the appropriate mechanical disadvantage is provided. Angle 338 can be determined by experimentation with a physical model or through mathematical modeling.

In generating a mathematical model, or in calculating torques generated by the weight and spring, the following will be helpful.

While, applicant prefers to select the measurement of angle through experimentation and iteration, it is believed that optimal angle can be determined generally using mathematical models of counterbalance arm 40. As explained above, first and second distal pivot axes 56 and 70, respectively, are displaced from one another by distance 208 (in the illustrated embodiment equal to 0.75"), shown in FIG. 3, and first and second and proximal pivot axes 54 and 66, respectively, are displaced from one another by displacement 72 (in the illustrated embodiment equal to 0.75"), shown in FIG. 4, substantially equal to distance 208. Displacement 72 is measure along diametrical line 190 and displacement 208 is measured along diametrical line 210. Diametrical line 210 is parallel or substantially parallel to rotation axis 58 which is presumed to be vertical. Distance 211 between diametrical line 210 and rotation axis 58 is fixed (in the illustrated embodiment 0.781"). Diametrical line 190 is parallel or substantially parallel to rotation axis 34 which is presumed to be vertical. Distance 191 between diametrical line 190 and rotation axis 34 is fixed (in the illustrated embodiment 0.781"). The weight of monitor arm assembly 50 and device 12 is assumed to act vertically downwardly along rotation axis 58. This assumption introduces slight error into the calculation as connections between the distal end of counterbalance arm 40 and components of monitor arm assembly 50 are not rigid. Assuming that counterbalance arm 40 is a weightless incompressible moment arm introduces little error to the mathematical modeling since monitor arm assembly 50 and device 12 are generally much more massive than counterbalance arm 40. Recognizing that some error is introduced into the mathematical model by these assumptions and other assumptions to be introduced later, optimal angle can be generally determined by assuming that spring force can be linearly modeled using Hooke's Law and that first and second parallel links act as components of moment arms to which the law of levers may be applied.

Figure 8:
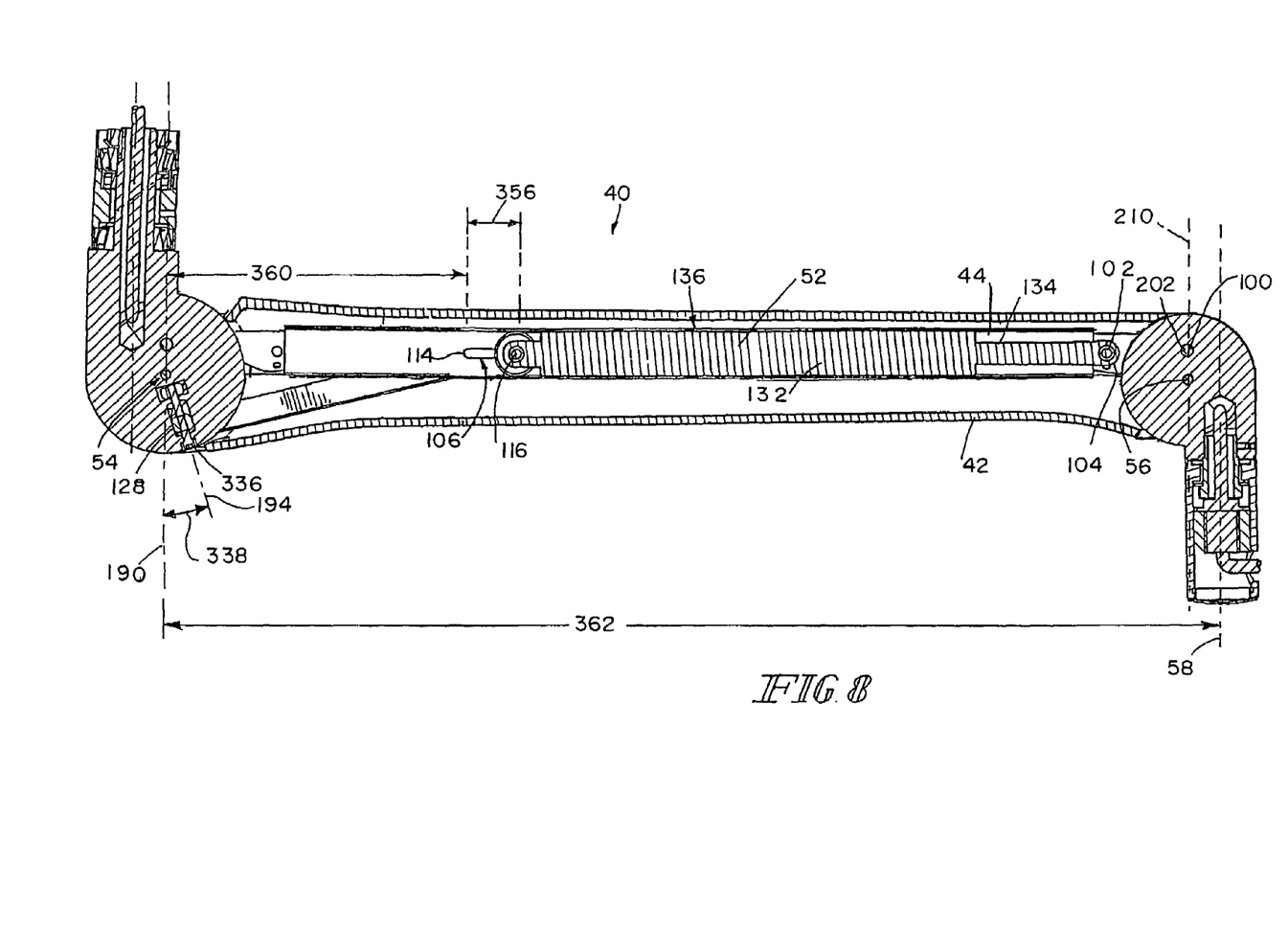
FIG. 8 is a cross-sectional view of the counterbalance arm of FIG. 7 showing the arm pivoted downwardly about the first proximal pivot axis so that the arm is in a substantially horizontal position.

Weight ("W") of monitor mount assembly 50 and device 12 is assumed to be a determinable constant acting vertically downwardly along rotation axis 58 to generate a torque about first proximal pivot axis 54. Thus weight acts on a moment arm having a length 362 ($L_{MA1}$), as shown in FIG. 8. Arm housing or first parallel link 42, arm weldment or second parallel link 44, proximal arm hub 38 and distal arm hub 48 are configured such that pivotal movement of counterbalance arm 40 about first proximal pivot axis 54 is limited. For example, the upper surface of arm housing or first parallel link 42 prohibits rotation of counterbalance arm 40 upwardly beyond a point at which upper surface of arm housing 42 would contact the outer surface of proximal hub 38 or bearing housing 36. In the illustrated embodiment, hub 38 and first parallel link 42 are formed to include stops (not shown) limiting pivotal movement of counterbalance arm 40 between an upper limit or raised position (wherein the arm angle θ is 38.68 degrees above horizontal or 51.32 degrees from vertical) and a lower limit or lowered position (wherein the arm angle θ is 38.68 degrees above horizontal or 128.68 degrees from vertical).

Weight of monitor mount assembly 50 and device 12 thus acts on a moment arm having the length ($L_{MA1}$) 362 of the distance ($L_{lp1}$) 55 (in the illustrated embodiment 26") between first proximal and distal axes 54 and 56, respectively, plus the additional distance required to extend this longitudinal axis to intersect rotation axis 58. Since rotation axis 58 and the diametrical line 210 through the first and second distal axes 56 and 70, respectively, is set at a fixed displacement (D) 211 (see FIG. 3) and the longitudinal axis forms an angle θ with the vertically oriented line 56 and axis 58, the additional distance is D/sin θ. Thus moment arm has a length 362 (see FIG. 8):

$$L_{MA1} = L_{lp1} + D/\sin \theta.$$

Since the weight acts vertically downwardly, the component of the weight perpendicular to the moment arm is W*sin θ. Thus the torque generated by the weight can be expressed:

$$\tau = -W^* \sin \theta^* (L_{lp1} + D/\sin \theta) = -(W^* L_{lp1} ^* \sin \theta + W^* D)$$

Referring again to FIGS. 3 and 5, to maintain equilibrium of the counterbalance arm 40, the force exerted by the gas spring 52 must generate a torque having the same magnitude in the opposite direction. The force (F) exerted by the gas spring 52 acts on connection pin 116 extending through slot 106 and connection pin-receiving aperture 124 in distal end 122 of spring link 46. Spring link 46 and connection pin 116 and top wall 108 of slot 106 act to reduce the spring force to a component along the longitudinal axis of the spring link 46 and a force perpendicular to the longitudinal axis 78 of second parallel link 44. Counterbalance arm 40 is formed to maintain longitudinal axis 78 of second parallel link 44 parallel to longitudinal axis 76 of first parallel link 42. Proximal hub 38 is formed to fix first and second proximal pivot axes 54, 66 so that second pivot axis 66 is always vertically above first pivot axis 54 and displaced from first pivot axis 54 by distance 72. Distal hub 48 is formed to fix first and second distal pivot axes 56, 70 so that second pivot axis 70 is always vertically above first pivot axis 56 and displaced from first pivot axis 56 by distance 208. In the illustrated embodiment, top wall 108 of slot 106 is displaced from longitudinal axis 78 of second parallel link 42 by a displacement of 0.125". This displacement is minimal compared to other relevant lengths, distances and displacements and may be ignored in modeling counterbalance arm 40 with little error introduction. The force perpendicular to the longitudinal axis 78 of second parallel link 44 generates a torque in the opposite direction from the torque generated by the weight W. Because of the parallel construction, the force perpendicular to the longitudinal axis 78 of second parallel link 44 may be treated for modeling purposes as a force perpendicular to the longitudinal axis 76 of second parallel link 42 and as generating a torque in the opposite direction from the torque generated by the weight W. However in order to satisfy this simplification, the focus of angle 332 must be displaced downwardly by the distance 72 between the first and second proximal pivot pins Those skilled in the art will recognize that when counterbalance arm 40 is in its lowered position, forming an angle of 128.68 degrees to the vertical, the weight of monitor arm assembly 50 and device 12 generates a torque about first proximal pivot axis 54 identical in magnitude to the torque generated when the counterbalance arm is in the raised position, forming an angle of 128.68 degrees to the vertical, because sin(51.32) is equal to sin(128.68). However, the angle formed between spring link 46 and second parallel link 44 decreases as counterbalance arm 40 rotates between its raised and lowered positions. The decrease of the angle formed between spring link 46 and second parallel link 44 causes the component of force perpendicular to second parallel link 44 to be decreased. Similarly, as counterbalance arm 40 pivots from raised position toward lowered position, the length of the moment arm at which the component of spring force perpendicular to second link acts increases, thereby reducing the torque generated proportionally.

Those skilled in the art will recognize that the device disclosed herein takes advantage of offsetting the third pivot axis 128 downwardly from the first and second proximal pivot axes 54 and 66, respectively and inwardly between the line 190 intersecting the first and second proximal pivot axes 54 and 66 and the line 210 intersecting the first and second distal pivot axes 56 and 70 respectively to provide a mechanical disadvantage to the combination of spring link 46 and spring 136 through the range of pivotal motion of counterbalance arm 40. Preferably the mechanical disadvantage compensates for the increased force exerted by spring 136 resulting from its further displacement from equilibrium during pivotal movement of counterbalance arm 40 between its upper limit of pivotal motion and its lower limit of pivotal motion. To the extent that the mechanical disadvantage does not completely compensate for the increased force exerted by spring 136, frictional forces inherent in the counterbalance arm 40 permit the counterbalance arm to maintain an equilibrium state at each orientation throughout its range of pivotal motion.

Referring to FIG. 6, counterbalance arm 40 is shown in the raised position with adjustment screw 336 rotated so that the third proximal pivot axis 128 is in its uppermost position causing the spring 136 to exert its strongest initial force. Whenever counterbalance arm 40 is in its raised position, i.e. at its upper limit regarding its pivotal movement about first proximal pivot axis 54, connection pin 116 extending through connection pin-receiving hole 124 in distal end 122 of spring links 46 is at a minimal displacement 350 from proximal end wall 114 of slot 106. The minimal displacement 350 of connection pin 116 from proximal end wall 114 differs depending on the location at which the third proximal pivot axis 128 is set. When the third proximal pivot axis 128 is set at its uppermost position, as shown, for example, in FIG. 6, the minimal displacement 350 of connection pin 116 from proximal end wall 114 of slot 106 is at a maximum value 352. Distal clevis 104 of rod 134 pivots about pivot pin 102 which is in a fixed position relative to arm weldment 44 and proximal clevis 130 of cylinder housing 132 is movable longitudinally with respect to arm weldment 44. Thus, when third proximal pivot axis 128 is in its uppermost position and the minimal displacement 350 of connection pin 116 from proximal end wall 114 is at its maximum value 352, the cylinder head within gas spring 52 has been urged by rod 134 to begin compressing gas in the cylinder housing 132 by a maximum initial value causing the force exerted by the gas spring 52 to be at a maximum initial value.

Referring to FIG. 7, counterbalance arm 40 is shown in the raised position with the adjustment screw 336 rotated so that the third proximal pivot axis 128 is in its lowermost position causing the spring 136 to exert its weakest initial force. When the third proximal pivot axis 128 is set at its lowermost position, as shown, for example, in FIG. 7, the minimal displacement 350 of connection pin 116 from proximal end wall 114 of slot 106 is at minimum value 354. Distal clevis 104 of rod 134 pivots about pivot pin 102 which is in a fixed position relative to arm weldment 44 and proximal clevis 130 of cylinder housing 132 is movable longitudinally with respect to arm weldment 44. Thus, when third proximal pivot axis 128 is in its lowermost position and the minimal displacement 350 of connection pin 116 from proximal end wall 114 is at its minimum value 354, the cylinder head within gas spring 52 has been urged by rod 134 to begin compressing gas in the cylinder housing 132 by a minimum initial value causing the force exerted by the gas spring 52 to be at a minimum initial value.

As shown for example, in FIG. 8, when counterbalance arm 40 is rotated downwardly about first proximal pivot axis 54, connection pin 116 extending through connection pin-slides receiving hole 124 in distal end 122 of spring links 46 and proximal clevis 130 of gas spring 52 slides longitudinally within slot 106 to increase a displacement 356 of connection pin 116 from proximal end wall 114 of slot 106. As the displacement 356 of connection pin 116 from proximal end wall 114 increases, rod 134 urges cylinder head of gas spring 52 further into cylinder housing 132 further compressing the gas in the cylinder and increasing the force exerted by the gas spring 52.

Figure 9:
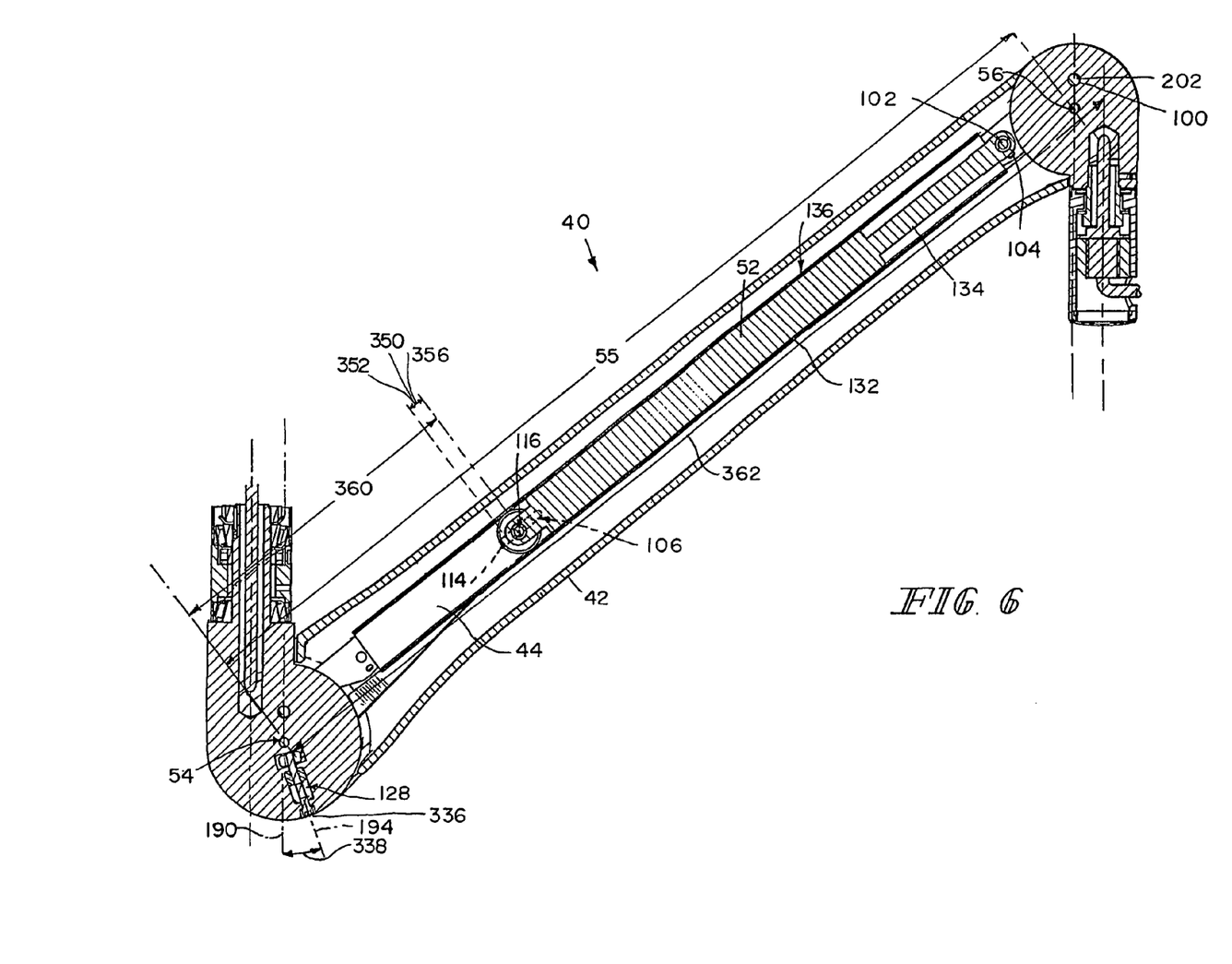
FIG. 9 is a cross-sectional view of the counterbalance arm of FIG. 7 showing the arm pivoted downwardly about the first proximal pivot axis so that the arm is in its lowered position.

As shown, for example, in FIG. 9, when counterbalance arm 40 is rotated downwardly about first proximal pivot axis 128 to its lowered position, connection pin 116 extending through connection pin-receiving hole 124 in distal end 122 of spring links 46 and proximal clevis 130 of gas spring 52 slides longitudinally within slot 106 so that the displacement 356 of connection pin from proximal end wall 114 of slot 106 reaches a maximum value 358. As the displacement 356 of connection pin 116 from proximal end wall 114 increases, rod 134 urges cylinder head of gas spring 52 further into cylinder housing 132 further compressing the gas in the cylinder and increasing the force exerted by the gas spring 52. Thus, when the displacement 356 reaches a maximum value 358, the force exerted longitudinally along arm weldment 44 by spring 136 reaches a maximum value for a set location of the third proximal pivot pin 126.

As shown in FIGS. 7–9, because first parallel link 42, second parallel link 44 and the fixed displacement 72 of first and second proximal pivot axes 54, 66, respectively, and first and second distal pivot axes 56, 70, respectively, create a parallelogram linkage, diametrical lines 190, 210 remain parallel throughout the pivotal range of counterbalance arm 40 about first proximal pivot axis 54. This permits monitor 14 mounted to monitor mount assembly 50 to remain properly oriented regardless of its vertical displacement from ceiling 20 of surgical suite.

As mentioned in the background, spring links 46, connection pin 116, slot 106 and gas spring 52 cooperate to urge connection pin 116 against upper wall 108 of slot 106 so that an upwardly directed vertical component of force is exerted at the location of connection pin 116 on second link 44. First parallel link 42 can be viewed as a lever with a fulcrum at the first proximal pivot axis 54. Thus, to facilitate vertical positioning of a device 12 connected to monitor mount assembly 50, it is desirable that the vertical component of force exerted by the connection pin 116 multiplied by the length 360 of the moment arm from the first proximal pivot axis 54 to the location of the connection pin 116 be equal to the vertical component of the force exerted by the weight of the monitor mount and device and the length 362 of the moment arm between the first proximal pivot axis 54 and rotation axis 58. Illustratively, angle 338 between radial line 194 and diametrical line 190 is determined based on the length of the spring links 46, the length 362 of the moment arm from first proximal pivot axis 54 to rotation axis 58, the displacement 72 between the first and second parallel links, and the force to stroke length characteristics of spring 136, so that the proper mechanical disadvantage is provided to cause the torque exerted by the weight of the monitor mount assembly 50 and device 12 to the counterbalance arm 40 to be substantially equal to, but opposite in direction from, the torque applied by the connection pin 116 through the upper wall 108 of the slot 106 to counterbalance arm 40.

Although the foregoing embodiment has been described, one skilled in the art can easily ascertain the essential characteristics of the apparatus, and various changes and modifications may be made to adapt the various uses and characteristics without departing from the spirit and scope of this application, as described by the claims which follow.

What is claimed is:

1. A counterbalance arm assembly comprising:
  a proximal hub formed to include a first proximal pivot axis extending therethrough, a second proximal pivot axis extending therethrough, and a third proximal pivot axis extending therethrough, said first, second and third proximal pivot axes being substantially mutually parallel, wherein the displacement between the first and third proximal pivot axes is adjustable,
  a distal hub having a first distal pivot axis extending therethrough and a second distal pivot axis extending therethrough,
  a first parallel link coupled at its proximal end for pivotal movement of the first parallel link relative to the proximal hub about the first proximal pivot axis and coupled at its distal end for pivotal movement of the first parallel link relative to the distal hub about the first distal pivot axis, a second parallel link coupled at its proximal end for pivotal movement of the second parallel link relative to the proximal hub about the second proximal pivot axis and coupled at its distal end for pivotal movement of the second parallel link relative to the distal hub about the second distal pivot axis, a spring coupled at its distal end to the second parallel link and at its proximal end to the second parallel link for longitudinal movement of the proximal end of the spring relative to the second link, a spring link coupled at its proximal end to the proximal hub for pivotal movement of the spring link about the third proximal axis, coupled at its distal end to the second parallel link for longitudinal movement of the distal end of the spring link relative to the second parallel link, and coupled at its distal end to the proximal end of the spring, wherein the proximal hub is formed to include an aperture extending radially from the first pivot axis and further comprising a pivot pin defining the third proximal pivot axis, said pin being slidably received in the aperture for movement of the pin radially with respect to the first proximal pivot axis, wherein a line intersecting the first and third proximal pivot axes is not colinear with and forms an angle with a line intersecting the first and second proximal pivot axes, wherein the first parallel link includes a longitudinal axis intersecting the first proximal and distal pivot axes, the second parallel link includes a longitudinal axis substantially parallel to the longitudinal axis of the first parallel link and intersecting the second proximal and distal pivot axes, the longitudinal axes of the first and second parallel links remain substantially parallel during movement of a device coupled thereto between a first elevation and a second elevation and the first longitudinal axis is between the second and third pivot axes.

2. The counterbalance arm assembly of claim 1 wherein a line intersecting the first and second distal pivot axes remains parallel to the line intersecting the first and second proximal pivot axes during movement of the device between the first elevation and the second elevation and the third proximal pivot axis is disposed between the line intersecting the first and second distal pivot axes and the line intersecting the first and second proximal pivot axes.

3. The counterbalance arm assembly of claim 2 wherein the first parallel link includes a housing having a cavity extending therethrough and a portion of the second parallel link is received in the cavity.

4. The counterbalance arm of claim 3 further comprising caps and plugs and wherein the first parallel link, caps, plugs, proximal hub and distal hub cooperate to form an enclosure around the second parallel link.

5. A surgical theater system for attachment to a structural component in a ceiling of a surgical suite, the surgical theater system comprising:

a hub configured to be mounted to the structural component and configured to rotate about a first vertical axis extending through the hub, a boom having a proximal end and a vertically-downwardly extending portion horizontally displaced from the proximal end terminating in a distal end, the boom being mounted at its proximal end to the hub, the vertically-downwardly extending portion having a second vertical axis extending therethrough, a proximal hub formed to include a first proximal pivot axis extending therethrough, a second proximal pivot axis extending therethrough, and a third proximal pivot axis extending therethrough, an aperture extending radially from the first pivot axis, and including a pivot pin defining the third proximal pivot axis slidably received in the aperture for movement of the pin radially with respect to the first proximal pivot axis whereby the displacement between the first and third proximal pivot axes is adjustable, the proximal hub being mounted to the vertically-downwardly extending portion of the boom for rotational movement of the hub about the second vertical axis, a distal hub having a first distal pivot axis extending therethrough and a second distal pivot axis extending therethrough, a first parallel link coupled at its proximal end for pivotal movement of the first parallel link relative to the proximal hub about the first proximal pivot axis and coupled at its distal end for pivotal movement of the first parallel link relative to the distal hub about the first distal pivot axis, a second parallel link coupled at its proximal end for pivotal movement of the second parallel link relative to the proximal hub about the second proximal pivot axis and coupled at its distal end for pivotal movement of the second parallel link relative to the distal hub about the second distal pivot axis, a spring coupled at its distal end to the second parallel link and at its proximal end to the second parallel link for longitudinal movement of the proximal end of the spring relative to the second link, a spring link coupled at its proximal end to the proximal hub for pivotal movement of the spring link about the third proximal axis, coupled at its distal end to the second parallel link for longitudinal movement of the distal end of the spring link relative to the second parallel link, and coupled at its distal end to the proximal end of the spring.

6. The surgical theater system of claim 5 wherein a line intersecting the first and third proximal pivot axes is not colinear with and forms an angle with a line intersecting the first and second proximal pivot axes.

7. The surgical theater system of claim 6 wherein the first parallel link includes a longitudinal axis intersecting the first proximal and distal pivot axes, the second parallel link includes a longitudinal axis intersecting the second proximal and distal pivot axes, the longitudinal axes of the first and second parallel links remain parallel during movement of a device coupled thereto between a first elevation and a second elevation and the first longitudinal axis is between the second and third pivot axes and a line intersecting the first and second distal pivot axes remains parallel to the line intersecting the first and second proximal pivot axes during movement of the device between the first elevation and the second elevation and the third proximal pivot axis is disposed between the line intersecting the first and second distal pivot axes and the line intersecting the first and second proximal pivot axes.

8. A counterbalance arm assembly comprising:

a proximal hub formed to include a first proximal pivot axis extending therethrough, a second proximal pivot axis extending therethrough, and a third proximal pivot axis extending therethrough, wherein a first line intersects the first and second proximal pivot axes and the displacement between the first and third proximal pivot axes is adjustable, a distal hub having a first distal pivot axis extending therethrough and a second distal pivot axis extending therethrough, wherein a second line intersects the first and second distal pivot axes and is substantially parallel to the first line, a first parallel link coupled at its proximal end for pivotal movement of the first parallel link relative to the proximal hub about the first proximal pivot axis and coupled at its distal end for pivotal movement of the first parallel link relative to the distal hub about the first distal pivot axis, the first parallel link having a first longitudinal axis intersecting the first proximal and distal pivot axes a second parallel link coupled at its proximal end for pivotal movement of the second parallel link relative to the proximal hub about the second proximal pivot axis and coupled at its distal end for pivotal movement of the second parallel link relative to the distal hub about the second distal pivot axis, the second parallel link having a second longitudinal axis intersecting the second proximal and distal pivot axes and is substantially parallel to the first longitudinal axis, a spring coupled at its distal end to the second parallel link and at its proximal end to the second parallel link for longitudinal movement of the proximal end of the spring relative to the second link, a spring link coupled at its proximal end to the proximal hub for pivotal movement of the spring link about the third proximal axis, coupled at its distal end to the second parallel link for longitudinal movement of the distal end of the spring link relative to the second parallel link, and coupled at its distal end to the proximal end of the spring, and wherein the third proximal pivot axis has a range of motion over which the third proximal pivot axis is always positioned so that the first longitudinal axis is between the second longitudinal axis and the third proximal pivot axis and so that the third proximal pivot axis is between the first line and the second line, whereby a mechanical disadvantage is provided to the coupled spring link and spring substantially compensating for increased spring forces resulting from further displacement from the spring's equilibrium length during pivotal movement of the counterbalance arm between a raised and a lowered position, and wherein the second distal link includes a longitudinally-extending slot and a connecting pin, said connecting pin extending laterally through the slot to couple the distal end of the spring link and the proximal end of the spring to the second parallel link.

9. The counterbalance arm of claim 8 wherein the first parallel link includes a housing having a cavity extending therethrough and a portion of the second parallel link is received in the cavity.

10. The counterbalance arm of claim 9 wherein the first parallel link, proximal hub and distal hub cooperate to enclose the second parallel link.

* * * * *